United States Patent [19]
Romanauskas

[11] Patent Number: 4,762,683
[45] Date of Patent: Aug. 9, 1988

[54] ANALYSIS DEVICE

[75] Inventor: William A. Romanauskas, Southbury, Conn.

[73] Assignee: E. I. Du Pont de Nemours and Company, Wilmington, Del.

[21] Appl. No.: 908,046

[22] Filed: Sep. 16, 1986

[51] Int. Cl.$^4$ .................. G01N 11/02; G01N 33/49; G01N 33/493

[52] U.S. Cl. ..................... 422/72; 422/102; 356/428

[58] Field of Search ............ 422/72, 64, 102; 436/45; 494/31–34; 356/244, 246, 427, 428

[56] References Cited

U.S. PATENT DOCUMENTS

| | | | |
|---|---|---|---|
| 3,555,284 | 1/1971 | Anderson | 250/218 |
| 3,744,975 | 7/1973 | Mailen | 23/259 |
| 3,795,451 | 3/1974 | Mailen | 356/246 |
| 3,798,459 | 3/1974 | Anderson | 250/218 |
| 4,123,173 | 10/1978 | Bullock et al. | 356/246 |
| 4,154,793 | 5/1979 | Guigan | 422/72 |
| 4,233,029 | 11/1980 | Columbus | 422/55 |
| 4,244,916 | 1/1981 | Guigan | 422/72 |
| 4,284,602 | 8/1981 | Kelton et al. | 422/72 |
| 4,387,164 | 6/1983 | Hevey et al. | 436/45 |
| 4,557,600 | 12/1985 | Klose et al. | 436/45 |
| 4,623,519 | 11/1986 | Cornut et al. | 422/72 |

FOREIGN PATENT DOCUMENTS

| | | |
|---|---|---|
| 0039825 | 11/1981 | European Pat. Off. . |
| 0052769 | 6/1982 | European Pat. Off. . |
| 0052770 | 6/1982 | European Pat. Off. . |
| 0169306 | 1/1986 | European Pat. Off. . |
| 2549961 | 4/1985 | France . |
| 2578054 | 8/1986 | France . |

Primary Examiner—Barry S. Richman
Assistant Examiner—Jill Johnston

[57] ABSTRACT

A centrifugal analysis device in which film capillaries communicate with peripheral cells, with a hydrophilic capillary providing the cell inlet and a hydrophobic capillary providing the cell outlet.

5 Claims, 2 Drawing Sheets

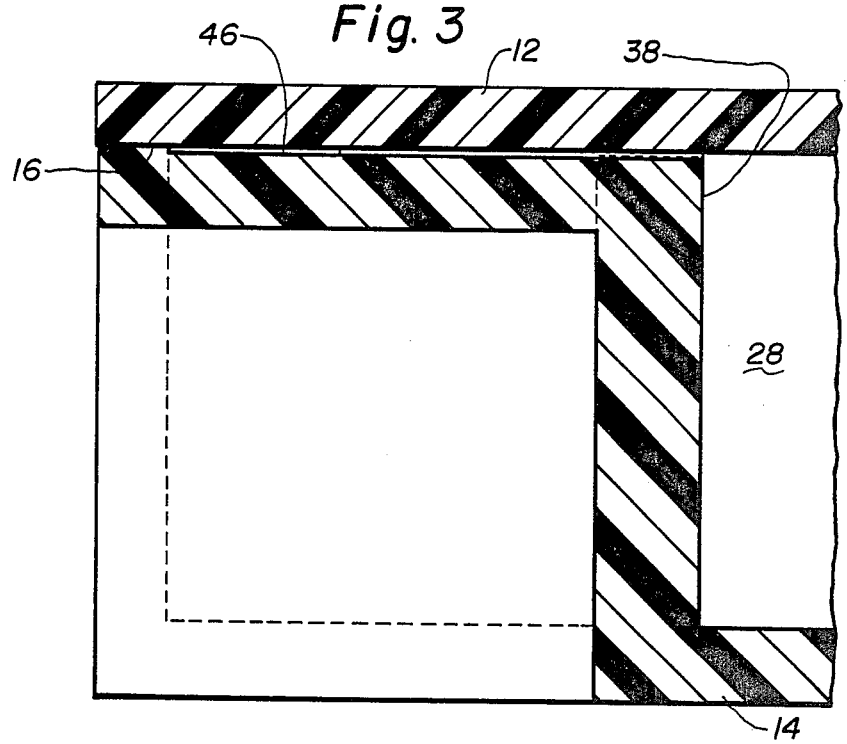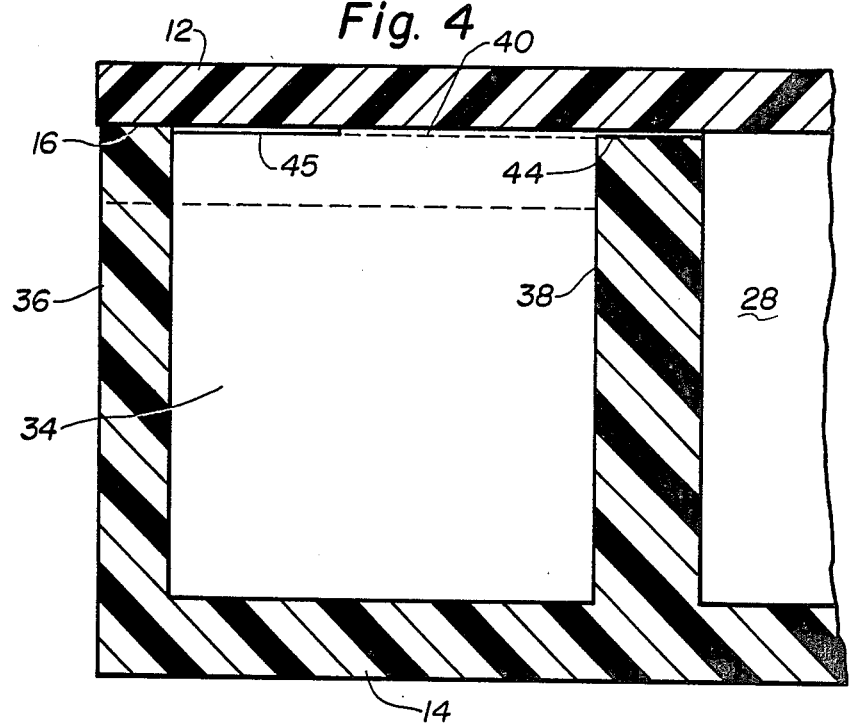

ANALYSIS DEVICE

CROSS REFERENCE TO RELATED APPLICATIONS

The invention described herein relates to an invention described in copending application Ser. No. 908,045, filed Sept. 16, 1986, "Analysis Device".

FIELD OF THE INVENTION

This invention relates to a centrifugal device for analyzing liquid samples.

BACKGROUND OF THE INVENTION

Many automatic analysis devices are known in which one or more liquid samples are introduced into a reagent-carrying rotor. Rotation of the rotor causes the displacement of the liquids to be analyzed towards the cells containing the reagents. Changes of the optical characteristics in the cells where the reaction takes place (changes in opacity, light absorption, color, refraction index, etc.) are measured. In this way, a series of measurements can be obtained which make possible the analysis of one or more samples.

In fact, older devices utilized cells mounted in series or in a descending series on a common support (sample cells, reagent cells, reaction cells) in which the sample moves from one cell to the other by any appropriate means, for example, by gravity. Several reagents and successive reaction cells can be utilized in this way. The proposal was then made to radially arrange these supports on a rotor to make use of the centrifugal force for the purpose of displacing the liquids (samples and possibly reagents) but each elementary support remained independent.

Rotors were conceived on which a series of supports with one or more radial series of cells were placed (see European applications Nos. 0 052 769 and 0 052 770 Boehringer Mannhein, for example). Also rotors without separate supports were used but provided for the introduction of the common central inlet followed by separated radial cells (see, for example, U.S. Pat. Nos. 3,744,957 Mailen and 3,798,459 Anderson). But most of these devices often only provided mediocre measurements as a result of nonuniformity of the dosages.

In one form of such centrifugal analyzers, dry reagents are held in small disposable cells located peripherally in a small disposable plastic rotor. The cells have optically clear top and bottom windows. Previously conditioned samples (typically of body fluids such as plasma or urine) are introduced into a receptacle in the center of the rotor. Since many of the reactions with the reagents are time dependent, it is required that the body fluids do not reach the reagents until desired. Centrifugal force is used to transfer the body fluids to the peripheral cells for analysis. To accomplish this transfer, the rotor is accelerated causing the body fluids to move centrifugally out to the cells and reagents. After a prescribed time the color changes are read optically to determine the results of the test. Since many cells (each with different reagents to perform a separate analysis) can be positioned in each rotor, the result is a fairly complete chemistry of the body fluid in a compact unit in a relatively short period of time.

Typical of these rotors are those described in U.S. Pat. Nos. 4,123,173, 3,555,284 and 4,387,164. While quite satisfactory for their intended purposes, these rotors do not fulfill the need that exists for a small disposable rotor that is capable of accurately providing many tests on a single sample. Disposable rotors of this type are described in a series of patents issued to Guigan. Typical of these patents are U.S. patent application Ser. No. 626,749 filed July 2, 1984 and U.S. Pat. No. 4,154,793. These rotors are comprised of two disk-like rigid plastic pieces secured together to form a closed rotor. The lower disk has a central hub for mounting on a rotor drive shaft and comprises a flat disk having a central receptacle and a plurality of peripheral cells formed therein. Each cell is separated from an adjacent cell by a raised radial ridge which forms sectors for each cell. A radial groove of capillary thickness dimensions extends from the central receptacle formed in the lower disk to the center, radially inner portion of each cell.

The top disk has a flat lower surface which is sealed to the radial ridges and periphery of the lower disk so as to provide the closed rotor. The rotor thus defines a plurality of small sectors each with a slit of capillary dimensions communicating with each cell from the central cavity. This rotor is a disposable unit adapted to receive a patient sample, through an opening in the center portion of the upper disk, which is retained in the central receptacle. The sample when subjected to centrifugal force is preferentially driven by the combined action of centrifugal force and capillary action to each sector to fill each cell. Air escapes from each cell through the groove formed in the lower disk.

One problem inherent in the Guigan design is that different chemistries, different dilutions or different fluids are necessary; therefore, more than one central receptacle is required. This is typically accomplished by placing a baffle in the central receptacle. Without the baffle all cells are subjected to the same pressure. With the baffle in the central cavity, due to acceleration, the cells nearest the leading edge of the baffle tend to be filled first. Also, it is sometimes difficult to fill all of the cells completely since the groove tends to become filled with liquid trying to exit the central receptacle under centrifugal force. This can result in filling the cells differently and difficulty in completely filling a particular cell with fluid from the central receptacle.

SUMMARY OF THE INVENTION

Many of the disadvantages of the prior art analysis devices are overcome by the centrifugal device of this invention in which a liquid sample may be analyzed by a device comprising a rotor having an axis of rotation, a central receptacle and a plurality of peripheral cells, each of the cells defining interiors, being adjacent two of the other cells and in fluid communication with the central receptacle, the receptacle and cells being defined by top and bottom plastic pieces secured to each other with the fluid communication provided by film capillaries formed between surfaces of the plastic pieces, the improvement wherein the film capillaries comprise a hydrophilic film capillary extending from the central receptacle radially between each of the adjacent cells, a first hydrophobic film capillary between the interior of each cell and the receptacle, and a second hydrophobic film capillary between each of the hydrophilic film capillaries and the interior of and one of the adjacent cells such that each of the cell interiors is in fluid communication with one of the hydrophilic film capillaries through one of the second hydrophobic film capillaries.

Preferably the second hydrophobic film capillary is located at a greater radial distance from the axis of rotation than the first hydrophilic film capillary. The device may have a third hydrophobic film capillary between each hydrophilic film capillary and the other adjoining cell such that there are two entrances for entering fluids into each cell through hydrophobic film capillaries on either side of the cell.

The device of this invention improves over many of the prior art devices in that separate passageways in the form of film capillaries are provided to permit the liquid to enter and leave each cell through separate paths.

BRIEF DESCRIPTION OF THE DRAWINGS

The invention may be more fully understood from the following detailed description thereof taken in connection with accompanying drawings which form a part of this application and in which:

FIG. 3 is a fragmentary, cross-sectional elevation view of the rotor device of FIG. 1 taken along the section line 3—3; and FIG. 4 is a fragmentary, cross-sectional elevational view of the rotor device of FIG. 1 taken along the section line 4—4 to particularly depict the structure of the hydrophobic outlet film capillary.

DESCRIPTION OF THE PREFERRED EMBODIMENT

Figure 1:
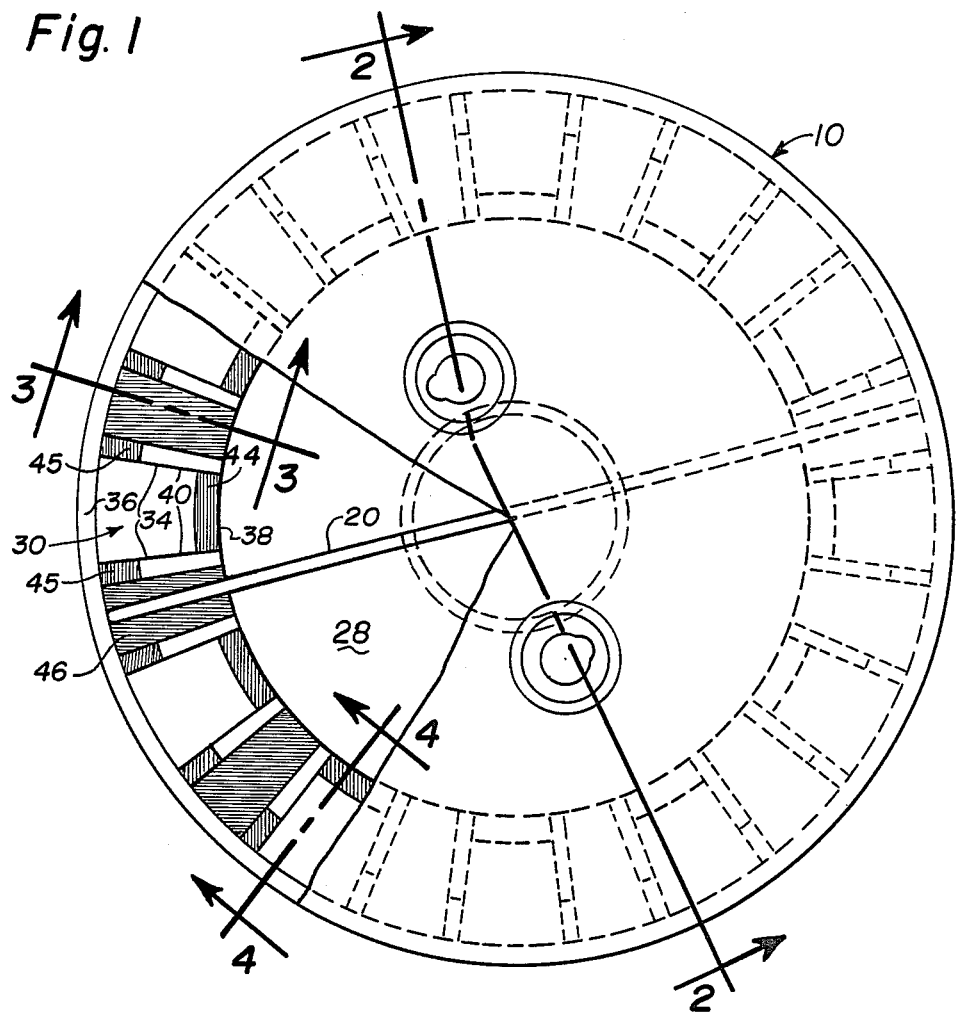
FIG. 1 is a plan view, partially cutaway, of an analyzer device constructed in accordance with a preferred embodiment of this invention.
Figure 2:
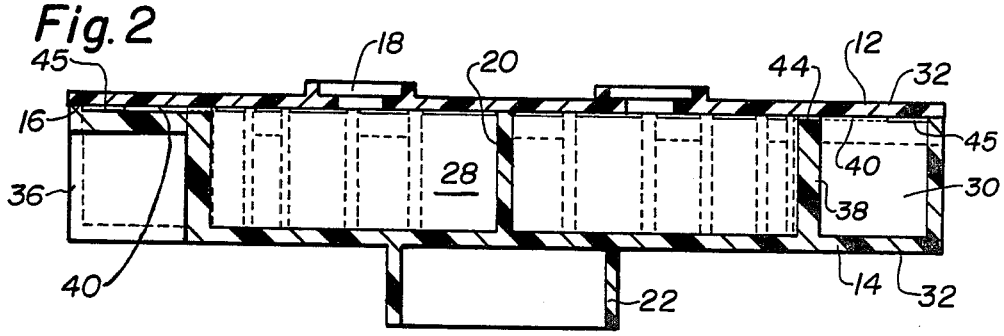
FIG. 2 is a cross-sectional view of the rotor device of FIG. 1 taken along the section line 2—2.

There may be seen in FIGS. 1 and 2 a centrifugal device that finds use in liquid analyses. This device comprises a plastic rotor 10 constructed from a top flat disk 12 and a bottom cup-like disk 14 having an outer rim 16 secured to the top disk 12 as by cementing, ultrasonic welding, thermal sealing or the like. The bottom disk 14 has a central receptacle 28 and peripheral cells 30 formed at the lower portion thereof and an annular mount 22 for mounting the disk on a centrifugal drive shaft (not shown). Ports 18 are formed in the top disk to provide access to the central receptacle 28. A vertical dividing septum 20 passes through the central portion of the receptacle 28 to divide the central receptacle into two portions, i.e., halves such that different fluid samples may be inserted for analysis in the respective portions.

The rotor itself is constructed of any suitable plastic that is chemically inert for the analyses to be performed, relatively rigid and optically transparent such that optical walls 32 may be formed in the upper and lower portion of each cell 30 for optical analysis of the cell's contents. Plastics suitable for this purpose include: polymethylmethacrylate, which is preferred, polycarbonate, polystyrene, and ionomer resin. Each cell 30 is defined by radial sidewalls 34, an outer wall 36 (topped by the rim 16) and an inner wall 38. The inner portion 40 of the radial walls 34 and the rim 16 are secured at their top as by heat sealing, ultrasonic bonding or the like to the top disk 12. The outer radial portions 45 of radial sidewalls 34 however are merely in contact therewith and are left in their rough state as results from the molding process. In this way the surface asperities and irregularities of the contacting surfaces of the top and bottom disk are sufficient to provide the required film capillaries 44, 45 and 46.

The disks forming the rotor itself are made of plastic materials whose surfaces are hydrophobic. If other than a hydrophobic material is used, the surfaces are treated in a known manner so that they are hydrophobic. Likewise the top of the inner wall 38 is simply in contact with the top disk 12 such that an outlet film capillary 44, which also has hydrophobic surfaces, is formed for each cell's access to the central receptacle 28.

Finally, the radial sidewalls 34 of the adjacent cells 30 are separated by regions of bottom disk 14. The regions have roughed top surfaces together with the top disk 12 form inlet hydrophilic film capillaries 46 (FIG. 3) between disks 12 and 14 which serve as inlets for the adjacent cells 30. This is accomplished by maintaining the bottom disk 14 at the region top surfaces simply in contact with a lower surface of the top disk 12. As noted, the surfaces are treated if the rotor is of a hydrophobic material such that this film capillary 46 has hydrophilic surfaces. Such treatments are well known in the art and need not be further described. The septum 20 preferably bisects a film capillary 46 on either side of the rotor.

With this construction, since the film capillary 46 is hydrophilic, sample liquid from the central receptacle is "wicked" out to the peripheral seal at the outer rim 16 through the hydrophilic film capillary 46 as soon as the liquid is exposed to the film capillary. This normally will occur after the sample is introduced into the central receptacle 28 of the rotor through one or another or both of the ports 18 and the rotor has begun to rotate. This rotation causes the liquid to reorient radially outward and the level to rise up to where it may contact the film capillaries 44 and 46. Continued rotation will cause the flow to begin through the radially outer film capillaries 45 to the cells 30 on either side. This preferential flow occurs because the inlet capillaries 45 are located at a larger radial distance than the outlet film capillary 44 provided at the inner wall 38. This statement assumes equal surface roughness on both surfaces. The early initiation of flow through the inlet capillary 45 thus will be prior to that through the outlet capillary 44 communicating directly with the cells 30. Such early flow may be further insured by forming the outer capillary 45 to have a relatively rougher surface than the other capillaries.

As fluid enters a cell 30, air is expelled through the outlet capillary 44 until all air is expelled from the cell. At this point, there is no further driving influence to force liquid from the cell and liquid is retained in the cell because of the hydrophobicity of the film capillaries 45 and 44.

The manner of treatment in order to make the various surfaces the plastic hydrophobic or hydrophilic is well known in the art and need not be recited here. Any known surface treatment may be accomplished as desired provided it meets the criteria of being chemically inert to the reactions taking place.

The rotor of this invention is seen to permit rapid and simultaneous filling of the cells. Each cell is filled completely with liquid leaving little or no air or gas to interfere with the optical measurement of the cells' contents. In addition, the liquid remains trapped within the cell even when rotation ceases (allowing static optical readings to be taken) or occurs at lower speeds than would otherwise be possible. Although the cells are depicted as rectangular in horizontal cross-section, it is to be understood that the cells preferably are cylindrical in shape.

What is claimed is:

1. In a centrifugal device for analyzing a liquid sample, the device comprising a rotor having an axis of rotation, a central receptacle and a plurality of cells circumferentially spaced about the periphery of the central receptacle each of the cells defining interiors and in fluid communication with the central receptacle, said receptacle and said cells being defined by top and bottom plastic disks secured to each other with fluid communication provided by film capillaries formed between adjacent surfaces of the disks, the improvement wherein the film capillaries comprise:

a plurality of hydrophilic film capillaries positioned in an annulus about the periphery of the central receptacle and extending radially between each of two circumferentially-spaced cells, a first plurality of hydrophobic film capillaries positioned in the annulus about the periphery of the central receptacle and extending circumferentially between each of said hydrophilic film capillaries and one of said circumferentially-spaced cells, a second plurality of hydrophobic film capillaries positioned in the annulus about the periphery of the central receptacle and extending radially between the central receptacle and each of the circumferentially spaced cells, such that the interior of each of the circumferentially-spaced cells is in fluid communication with one of said hydrophilic film capillaries through one of said first plurality of hydrophobic film capillaries.

2. The device of claim 1, wherein the improvement further comprises each of said first plurality of hydrophobic film capillaries being located at a greater radial distance from the axis of rotation than each of said second plurality of hydrophobic film capillaries.

3. The device of claim 2, wherein the improvement further comprises a third plurality of hydrophobic film capillaries positioned in the annulus about the periphery of the central receptacle and extending circumferentially between each of said hydrophilic film capillaries and another of said circumferentially-spaced cells.

4. The device of claim 1, wherein the improvement further comprises a third plurality of hydrophobic film capillaries positioned in the annulus about the periphery of the central receptacle and extending circumferentially between each of said hydrophilic film capillaries and another of said circumferentially-spaced cells.

5. The device of claim 4, wherein the improvement further comprises each of said first plurality of hydrophobic film capillaries being located at a greater distance from the axis of rotation than each of the second plurality of hydrophobic film capillaries.

* * * * *